United States Patent [19]
Hamblen

[11] Patent Number: 5,152,787
[45] Date of Patent: Oct. 6, 1992

[54] INTRAOCULAR GRADIENT-INDEX LENSES USED IN EYE IMPLANTATION

[75] Inventor: David P. Hamblen, Rochester, N.Y.

[73] Assignee: Eastman Kodak Company, Rochester, N.Y.

[21] Appl. No.: 629,893

[22] Filed: Dec. 19, 1990

[51] Int. Cl.⁵ .............................................. A61F 2/16
[52] U.S. Cl. ............................. 623/6; 351/160 R; 351/161; 264/1.7; 264/2.1; 623/901
[58] Field of Search ............... 623/6, 901; 351/160 R, 351/161, 168

[56] References Cited

U.S. PATENT DOCUMENTS

| | | | |
|---|---|---|---|
| Re. 33,039 | 8/1989 | Arnott | 623/6 |
| 4,022,855 | 5/1977 | Hamblen | 264/1 |
| 4,087,866 | 5/1978 | Choyce et al. | 623/6 |
| 4,441,217 | 4/1984 | Cozean, Jr. | 623/6 |
| 4,504,982 | 3/1985 | Burk | 623/6 |
| 4,513,456 | 4/1985 | White | 623/6 |
| 4,524,468 | 6/1985 | Kelman | 623/6 |
| 4,536,897 | 8/1985 | Powell | 623/6 |
| 4,615,701 | 10/1986 | Woods | 623/6 |
| 4,664,666 | 5/1987 | Barrett | 623/6 |
| 4,666,249 | 5/1987 | Bauman et al. | 351/160 |
| 4,666,640 | 5/1987 | Neefe | 264/2.1 |
| 4,769,033 | 9/1988 | Nordan | 623/6 |
| 4,813,955 | 3/1989 | Achatz et al. | 623/6 |

FOREIGN PATENT DOCUMENTS

| | | |
|---|---|---|
| 0308705A2 | 9/1988 | European Pat. Off. . |
| 0329981A1 | 1/1989 | European Pat. Off. . |
| WO86/03961 | 7/1986 | PCT Int'l Appl. ................ 623/6 |
| WO87/07496 | 12/1987 | PCT Int'l Appl. ................ 623/6 |
| 2151371 | 7/1985 | United Kingdom ................ 623/6 |

OTHER PUBLICATIONS

"Dual Vision Lenses Give A Better View", by J. Hecht, *New Scientist*, 1990 623-626.

Primary Examiner—Ronald Frinks
Attorney, Agent, or Firm—Charles E. Snee, III.

[57] ABSTRACT

The present invention relates to implants (intraocular lenses) for implantation in the human eyeball to replace the natural crystalline lens. In general, the implant includes a body which includes anterior and posterior surfaces, an axis, and a periphery. The body is formed of a transparent material having an index of refraction which varies with a predetermined profile from the axis to the periphery of the body. In a first embodiment, the body is formed of one element having a convex-convex shape and an index of refraction which decreases in the direction away from the axis of the body. For dual-focus capabilities, the body has an inner and an outer zone with separate gradient profiles and surface curvatures, or an inner zone which is offset from the axis and is the center of the gradient profile. The inner and outer zones provide focusing for nearby and distant objects respectively. In a second embodiment, the implant includes an achromatic doublet lens of first and second contacting elements formed of a transparent material. The transparent materials of the first and second elements have gradient indices of refraction which decrease in opposite directions from each other between the axis to the periphery of the lens. Haptics extend from the periphery of each implant for engagement with appropriate portions of the eyeball.

4 Claims, 4 Drawing Sheets

INTRAOCULAR GRADIENT-INDEX LENSES USED IN EYE IMPLANTATION

FIELD OF THE INVENTION

The present invention relates to intraocular lenses for implantation into the human eye.

BACKGROUND OF THE INVENTION

In cataract surgery, the crystalline lens or lens nucleus from the eye is removed and, most commonly, an artificial lens is implanted within the eye. When implanted, the lens is supported in either the anterior or posterior chamber of the eye by support means, such as one or more struts, that extend outwardly from the artificial lens.

U.S. Pat. No. 4,441,217 discloses various arrangements for intraocular lenses having a light focusing lens body with oppositely disposed support members. When implanted in the human eye, the support members contact natural regions of the eye and position the optical axis of the lens body at a point that is offset from the geometric center axis of the cornea. With such positioning, the optical axis of the lens is aligned with the pupillary axis of the eye. For other intraocular lens configurations see, for example, U.S. Pat. Nos. 4,513,456; 4,536,897; and 4,664,666.

The article entitled "Dual Vision Lenses Give a Better View" by J. Hecht in *New Scientist*, Mar. 10, 1990, at page 39, discloses a coated implant lens designed by the 3M Company that focuses on both near and distant objects. The lens uses a technology called "binary" or "diffractive" optics whereby light waves are scattered around the edges of objects in their path. The direction of scattering depends on both the shape of the object and the wavelength of light. The 3M lens is described as having one-half of a back surface covered with a series of stepped ridges (grating) which are no more than two micrometers high. This series of ridges combines with the refractive power of the lens to focus light from nearby objects onto the retina. Other areas of the lens not having a series of ridges focus light from distant objects onto the retina. It is explained that the brain ignores the out-of-focus light reaching the retina. In other words, the brain is capable of automatically shifting and discriminating between the two images. Therefore, the ridged lenses permit a patient to focus on both near and distant objects as if they were wearing bifocals. This avoids the need for patients to wear glasses to see nearby objects as normally required with the previously used plastic lenses.

The grating design of the 3M dual-focus lens is similar to a diffraction grating to control light spreading and to cause light to converge at a common focal point. Such diffraction grating at the various portions of the 3M lens degrades the lens, which degradation can be reduced by supplying finer and finer gratings. With diffraction optics only a small area of the 3M lens does the focusing. More particularly, light incident on the front surface of the 3M lens passes therethrough in normal fashion, and diffraction only takes place at the sharp edge of a ridge. Therefore, it is preferable to provide as many sharp ridges in the space of the 3M lens as possible to provide the diffractive focusing. However, a normal lens implant has a maximum diameter of about 5 mm, with most lenses being less than that, and only a limited quantity of ridges can be supplied in the 3M lens. In light of the above discussion, it appears that the 3M lens is somewhat expensive to manufacture in order to provide the required series of miniature ridges in the proper places on the very small lens implants. Therefore, it is desired to provide a dual-focus lens for implantation in the human eye which avoids the degradation produced by diffraction optics and can be easily and inexpensively manufactured.

SUMMARY OF THE INVENTION

The present invention is directed to an implant (intraocular lens) for implantation in the human eye after cataract extraction which uses refractive optics. The implant comprises an optical body comprising anterior and posterior surfaces, an axis through the anterior and posterior surfaces, and a periphery between the anterior and posterior surfaces. The optical body is formed of a transparent material having a varying gradient index of refraction of a preselected profile between the axis and the periphery. With such varying gradient index of refraction, light is continuously refracted as it progresses through the body from the anterior surface to the posterior surface by the varying refractive index within the body.

In a first embodiment of the implant of the present invention, the body of the intraocular lens comprises a convex-convex shape and is formed of a transparent material having an index gradient which decreases in the direction from the axis to the periphery of the body to provide for aberration correction.

In a second embodiment, the optical body is divided into an inner and an outer zone which are centered about the axis of the anterior and posterior surfaces. Each of the anterior and posterior surfaces of the inner and outer zones have separate radii of curvature for focusing nearby and distant objects, respectively, onto the retina of the eyeball. The transparent material of the inner and outer zone comprise a homogeneous material, or the inner and outer zones comprise a varying gradient index of refraction of a first and a second predetermined profile, respectively. With either arrangement, the inner zone will cause rays of light from only nearby objects to be focused on a retina of the eyeball, while the outer zone will cause rays of light from only distant objects to be focused on a retina of the eyeball.

In a third embodiment of the present implant, the body is a doublet lens comprising a first and a second element. The first element comprises a first surface forming the anterior surface of the body, and a second surface. The second element comprises a first surface which is coupled to the second surface of the first element, and a second surface forming the posterior surface of the body. Additionally, the varying index of refraction of the material of the body increases from the axis of the body to the periphery in one of the first and second elements, and decreases from the axis to the periphery in the other of the first and second elements.

The invention will be better understood from the following more detailed description taken with the accompanying drawings and claims.

BRIEF DESCRIPTION OF THE DRAWINGS

The drawings are not necessarily to scale, and corresponding elements in the various figures have the same numerical designation.

DETAILED DESCRIPTION

Figure 1:
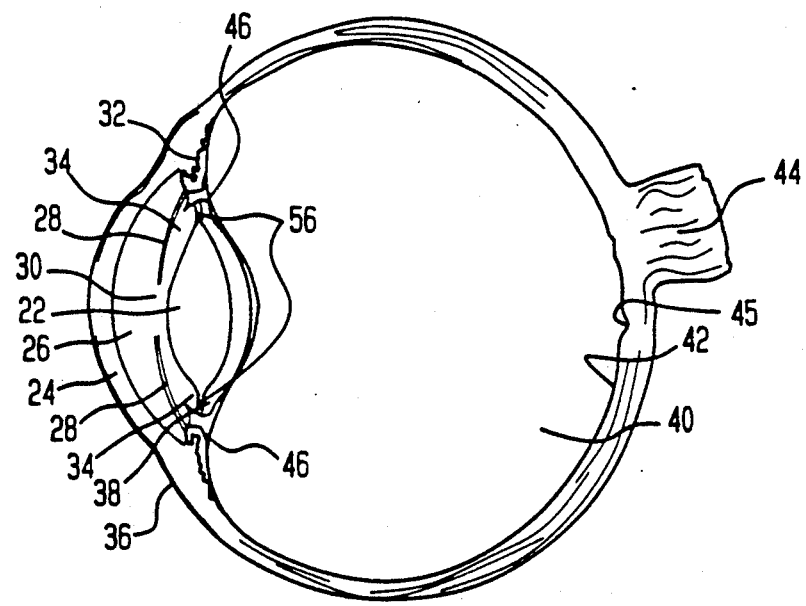
FIG. 1 is a top horizontal sectional view through the center of a human eye with an implant in accordance with the present invention with a ciliary sulcus placement.

Referring now to FIG. 1, there is shown a top sectional view through the center of a human eyeball 20 with an implant (intraocular lens) 22, in accordance with the present invention, substituted for an original crystalline lens (not shown). As is known, the human eyeball 20 includes a cornea 24 which has a single layer of endothelial cells (not shown) on its inner surface. The cornea 24 is the projecting transparent part of an external tunic of the eyeball 20. Behind the cornea 24 is an anterior chamber 26 which is filled with an aqueous fluid. At the rear of the anterior chamber 26 there is an iris 28 which defines a pupil 30 at the center thereof. The iris 28 is a thin circular-shaped, contractile curtain, suspended in the aqueous fluid behind the corena 24, and functions to contract and expand to adjust the amount of light passing through the pupil 30. At its outer periphery, the iris 28 is connected to a ciliary sulcus 32 which includes the ciliary muscle (not shown) that adjusts the original crystalline lens and, in turn, the eyeball 20 for the vision of near objects. More particularly, when the eye is at rest the ciliary muscle is relaxed and the original crystalline lens is adapted for distant vision whereby a distant image is focused on the retina 42. When light rays from a near object approach the eyeball 20, the ciliary muscle (not shown) causes an increase in the refracting power of the original crystalline lens by compressing the lens to increase the convexity of the anterior (front) surface of the lens (adjacent the iris 28). The posterior (back) surface of the original crystalline lens alters (increases curvature) only very slightly with the main change in the curvature of the lens taking place at the front surface of the lens to increase its thickness and radius of curvature. In this manner near objects are focused onto the retina.

The region behind the iris 28 forms a posterior chamber 34 which also contains the aqueous fluid. The implant 22 is mounted in the posterior chamber 34 and is held in position by engagement in the ciliary sulcus 32. Outwardly of the ciliary sulcus 32 is the white 36 of the eyeball 20. To the rear of the posterior chamber 34 is the posterior capsule 38 which contains the aqueous fluid. Behind the posterior capsule 38 is a cavity 40 whose inner wall is the retina 42 of the eyeball 20. The cavity 40 is filled with a vitreous humor having a consistency of a thin jelly. Each of the aqueous fluid and the vitreous humor of the eyeball 20 have approximately the same refractive index. An optic nerve 44 extends from the rear (to the nasal side) of the eyeball 20 to carry light stimulated impulses incident on the retina 42 to the brain. More detailed pictures and discussions of the human eyeball can be found in, for example, the book entitled *Grays Anatomy*, at pages 824–843, and other books on geometrical optics.

During cataract extraction, the original crystalline lens is removed and the implant 22 is substituted therefor. The original crystalline lens is normally a transparent, biconvex body, the convexity being greater on the posterior surface than on the anterior surface. The original crystalline lens consists of concentric layers, of which the external layers are soft, the intermediate layers are firmer, and the central layers form a hardened nucleus. The original crystalline lens is encircled by a ciliary processes 46 (see FIG. 1) of the ciliary sulcus 32. In general, implants are formed of a solid homogenous transparent material and, once implanted in the posterior chamber 34, cannot be altered in shape by the ciliary muscle. Therefore, prior art implants are primarily useful for providing improved distance vision, and glasses are needed for providing near vision.

Figure 2:
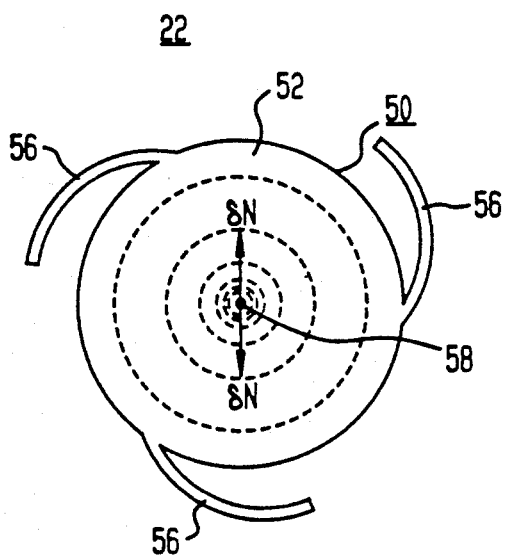
FIG. 2 is a front elevational view of an implant with a gradient index in accordance with the present invention.
Figure 3:
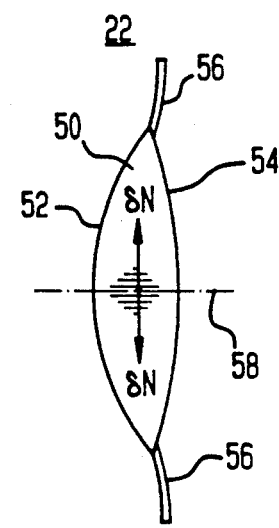
FIG. 3 is a side elevational view of the implant of FIG. 2.

Referring now to FIGS. 2 and 3, FIG. 2 shows an enlarged front elevational view of the implant 22 in accordance with a first embodiment of the present invention, while FIG. 3 shows an enlarged side elevational view of the implant 22 of FIG. 2. The implant 22 comprises a disc shaped intraocular lens 50 (an optical body) having a convex anterior surface 52, and a convex posterior surface 54 (shown only in FIG. 3). In accordance with the present invention, the lens 50 is formed of a transparent material formed of plastic having a continuous change of refractive index that varies in a direction orthogonal to a central optical axis 58. The lens 50 also comprises haptics 56 which extend from the lens 50 and serve to engage the ciliary sulcus 32 for holding, and preventing the rotation of, the implant 22 behind the pupil 30 of the eyeball 20. The haptics 56 can comprise any suitable shape to hold the implant 22 in the eyeball 20.

The surfaces 52 and 54 are curved in a known manner to give the lens 50 the desired power and other optical characteristics. Both of the surfaces 52 and 54 are curved such that light from near and distant objects which is incident on the anterior surface 52 of the lens 50 is brought to focus on the retina 42 of the eyeball 20. Such focusing is caused by refraction at the surfaces 52 and 54 and the bending of light rays (not shown) within the graded refractive index of the material of the lens 50. The curved anterior and posterior surfaces 52 and 54, respectively, of the lens 50 have in common the central optical axis 58.

Figure 4:
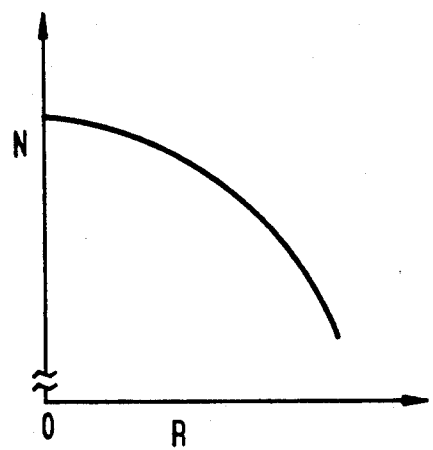
FIG. 4 is a plot relating to the refractive index of the material of the implant of FIGS. 2 and 3.

Referring now to FIG. 4, there is shown a plot (x-y graph) relating to a change in refractive index, N, of the material of lens 50 of FIGS. 2 and 3 on the y-axis versus a radial distance from the axis 58 of the lens 50 on the x-axis. More particularly, the highest index of refraction occurs in the area of the optical axis 58 and decreases in a parabolic manner to the outer edge of the intraocular lens 50. The lens 50 with the gradient index therein is an improvement over prior art homogeneous material implants having a shape as shown in FIGS. 2 and 3, because the lens 50 corrects for aberrations (e.g., spherical aberration) normally found in the prior art implants. Such lens 50, however, does not provide dual focusing capabilities. Dual-focusing lenses in accordance with the present invention can be provided in various ways.

Figure 5:
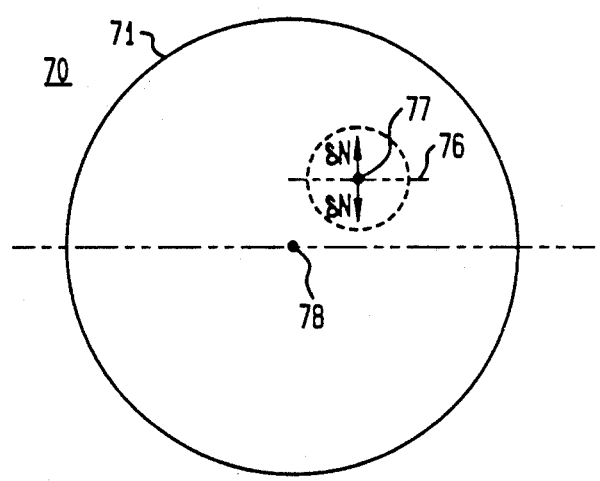
FIG. 5 is a front elevational view of a dual-focus gradient index implant with an inner element for focusing near objects in accordance with the present invention.
Figure 6:
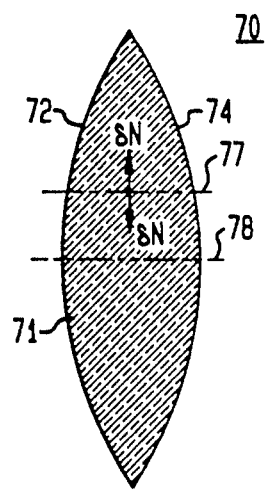
FIG. 6 is a top elevational view of the implant of FIG. 5.

Referring now to FIGS. 5 and 6, FIG. 5 shows an enlarged front elevational view of a dual-focusing implant 70 in accordance with a second embodiment of the present invention, while FIG. 6 shows an enlarged side elevational view of the implant 70 of FIG. 5 with the anterior and posterior surfaces 72 and 74, respectively. Implant 70 comprises a gradient index lens 71 with an inner zone 76. The inner zone 76 comprises an axis 77 which centers the gradient index (similar to the profile shown in FIG. 4) of both the inner zone 76 and the lens 71. It is to be understood that the axis 77 of the inner zone 76 is offset by a predetermined amount from an axis of curvature 78 of the lens 71 in order to image nearby objects in front of the eyeball 20 onto a fovea centralis 45 of the retina 42. The fovea centralis 45 is located approximately 3 mm from the optic nerve 44 in a direction towards an adjacent ear, and is the part of the retina where vision is most acute. The anterior and posterior surfaces 72 and 74, respectively, can be reshaped after casting or molding to provide a curvature for surfaces 72 and 74 that focuses light rays from distant objects (which are incident on the area outside inner zone 76) onto the retina 42. It is to be understood that haptics (not shown) of any suitable design are included for the implant 70.

Figure 7:
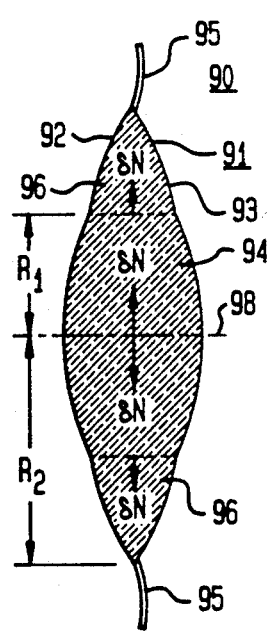
FIG. 7 is a top elevational view of a preferred dual-focus implant having an inner and outer gradient index zone in accordance with the present invention.

Referring now to FIG. 7, there is shown an enlarged side elevational view of an implant 90 in accordance with a third embodiment of the present invention. Implant 90 comprises a lens 91 with an anterior and a posterior surface 92 and 93, respectively, and haptics 95. Both an inner zone 94 and an outer zone 96 of the lens 91 are centered on an optical axis 98. In a first variation of the implant 90 of FIG. 7, the lens 91 is formed of a homogeneous material with a predetermined index of refraction. The anterior and posterior surfaces 92 and 93, respectively, in the area of the inner zone 94 are shaped to focus objects located immediately in front of the eyeball 20 onto the retina 42. Additionally, the anterior and posterior surfaces 92 and 93, respectively, in the area of outer zone 96 are shaped to focus distant objects located in front of the eyeball 20 onto the retina 42. Because of the shape of the anterior and posterior surfaces 92 and 93, respectively, light from distant objects incident on the inner zone 94, and light from nearby objects incident on the outer zone 96, are not focused on the retina 42.

In a second embodiment and a preferred variation of the implant 90 of FIG. 7, the lens 91 is formed of material wherein each of the inner and outer zones 94 and 96, respectively, has a separate index gradient. The inner zone 94, with a radius $R_1$, is formed with a predetermined index gradient and has a curvature of each of the anterior and posterior surfaces 92 and 93, respectively, for causing nearby objects to be focused onto the retina 42. The outer zone 96, disposed in the annular area of radius $R_2-R_1$, is formed with a predetermined separate index gradient, and has a curvature of each of the anterior and posterior surfaces 92 and 93, respectively, for causing distant objects to be focused onto the retina 42.

Figure 8:
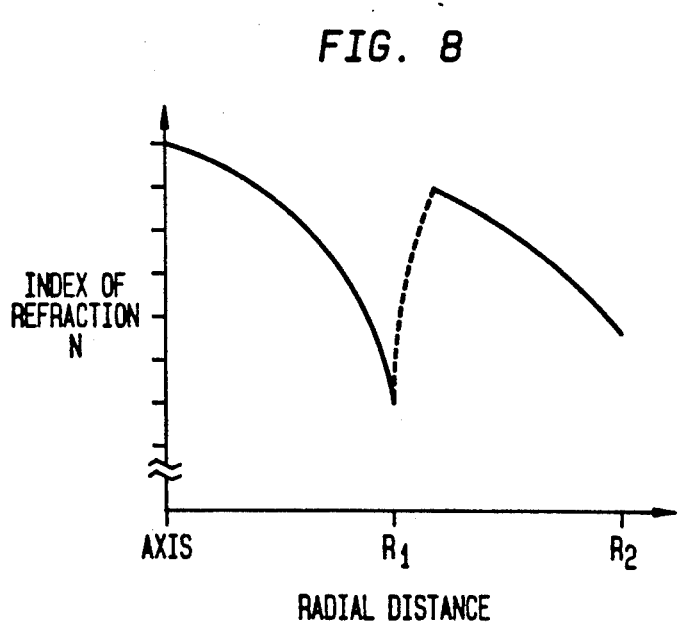
FIG. 8 is a plot relating to the refractive index of the material of the implant of FIG. 7.

Referring now to FIG. 8, there is shown a plot (x-y graph) relating to a refractive index, N, of the material of lens 91 of FIG. 7 on the y-axis versus a radial distance from the axis 98 of the lens 91 on the x-axis.

As shown in FIG. 8, the inner zone 94 includes a parabolically decreasing gradient index from the axis 98 to radius $R_1$. At the boundary of the inner zone 94 and outer zone 96, the refractive index is increased and then decreases parabolically in the outer zone 96 between the radii $R_1$ and $R_2$. Exemplary data for a lens 91 are:

$R_1$ = 2.8 mm;

$R_2$ = approximately 4.5 mm;

the maximum index N of inner zone 94 = 1.56 decreasing parabolically from axis 98 to N = approximately 1.4925;

the maximum index N of outer zone 96 = approximately 1.55 at $R_1$ decreasing parabolically to N = approximately 1.51 at $R_2$.

Figure 9:
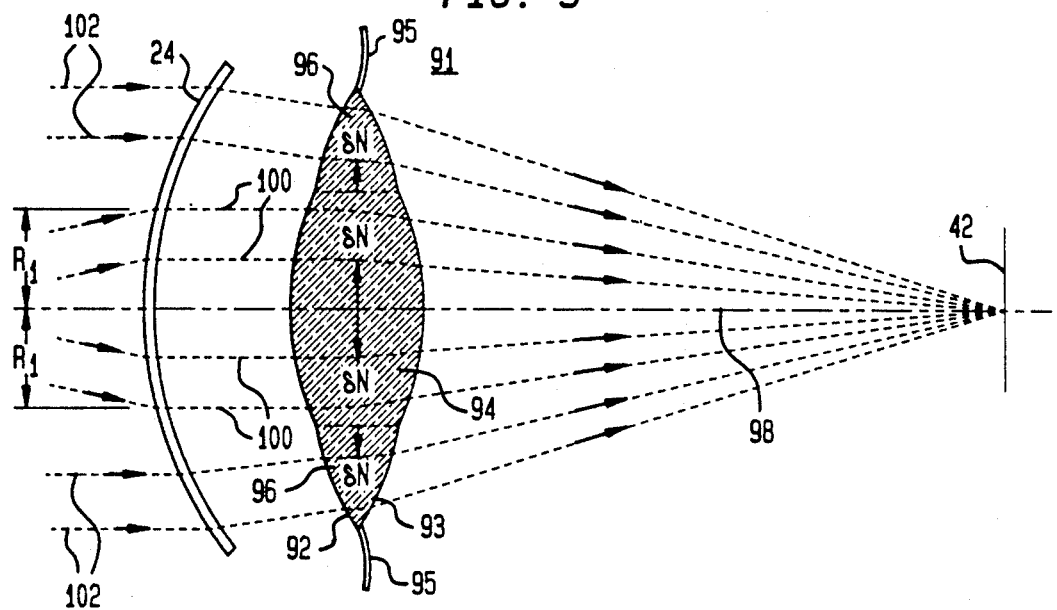
FIG. 9 is a side sectional view of a portion of the eyeball showing traces of light rays from near and distant objects through the cornea and through the inner and outer zones, respectively, of the implant of FIG. 7, and onto the retina.

Referring now to FIG. 9, there is shown a side sectional view of a portion of the eyeball 20 showing tracings of light rays 100 from nearby objects, and tracing of light rays 102 from distant objects, passing through the cornea 24, then through the inner zone 94 and the outer zone 96, respectively, of the lens 91 of FIG. 7, and onto the retina 42. More particularly, the diverging light rays 100 from nearby objects are refracted by the cornea 24 and are substantially collimated. The substantially collimated light rays 100 are incident on anterior surface 92 of the inner zone 94 of lens 91, are bent by the gradient index therein, and are focused onto the retina 42. Similarly, the nearly parallel light rays 102 arriving from distant objects are refracted by the cornea 24 and become slightly convergent. The slightly converging light rays 102 are incident on the anterior surface of the outer zone 96 of lens 91, are bent by the gradient index therein, and are focused onto the retina 42. Therefore, lens 91 is a dual-focus lens.

Figure 10:
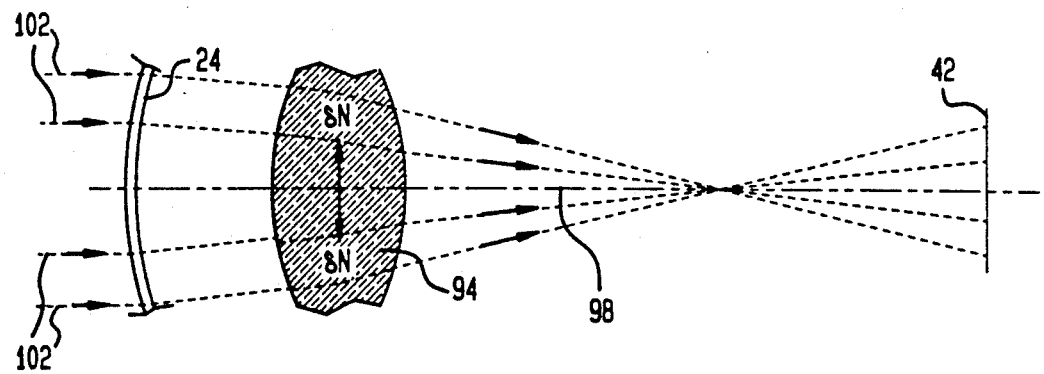
FIG. 10 is a side view of a portion of the eyeball showing traces of light rays from distant objects through the cornea and through the inner zone of the implant of FIG. 7, and onto the retina.

Referring now to FIG. 10, there is shown a side sectional view of a portion of the eyeball 20 showing tracings of light rays 102 from a distant object which pass through the cornea 24, and then through the inner zone 94. More particularly, the nearly parallel light rays 102 from the distant object are refracted by the cornea 24 into slightly converging light rays 102 which are incident on the anterior surface 92 of the inner zone 94. In passing through the inner zone 94, the light rays are bent towards the optical axis 98 and are focused to a point well in front of the retina 42 before diverging and becoming incident on the retina 42. Although not shown in FIGS. 9 and 10, it is to be understood that light rays 100 (only shown in FIG. 9) from a nearby object that pass through the cornea 24 and are incident on the anterior surface 92 of the outer zone 96 are focused to a point well behind the retina 42. The brain distinguishes between the light rays 100 and 102 to provide near and far vision, and avoids interference of the rays 100 and 102 that are not focused on the retina 42. Therefore, the lens 91 is a dual-focusing lens where light rays 100 from near objects are focused by the inner zone onto the retina, and light rays 102 from distant objects are focused by the outer zone 96 onto the retina 42. In other words, the gradient index in the inner zone 94 of the lens 91 provides strong correction for focusing near objects onto the retina 42, while the outer zone 96 of lens 91 provides weaker correction for focusing distant objects onto the retina 42.

For each of the dual-focusing lenses 71 and 91, the brain performs automatic shifting and discriminating between the near and distant objects as explained in the article by J. Hecht in the *New Scientist* of Mar. 10, 1990 at page 39 disclosed hereinbefore. In the graded intraocular lenses 50, 71 and 91, the material composition is such that it is inert and resists ingrowth of vascular tissue of the eyeball 20. The lenses 50, 71 and 91 can be a rigid body. However, to prevent irritation due to pressure on the ciliary processes 46, the lens 50 is preferably constructed as a less rigid lens which has the ability of complete restitution to its molded shape following some flexure. It is to be understood that the hardness of a lens can be controlled by a polymerization process used in manufacturing the lens. More particularly, certain lenses made by a spin-molding process (described hereinafter) can be slightly flexible depending on the materials used to make such lenses.

Used as a replacement lens following cataract extraction, the lenses 50, 71 and 91 have the advantage over a conventional plastic singlet lens in providing aberration correction by means of its radially deposited index gradient(s). Improvements in focusing are made by lenses 50, 71 and 91 by correcting for aberrations of spherical, coma and astigmatism over that which can be accomplished with a biconvex lens of homogeneous composition.

Fabrication of the graded index lenses 50, 71 and 91 is preferably accomplished by a spin-molding technique disclosed in U.S. Pat. No. 4,022,855. There, a reusable mold, for example, of silicone rubber, is made defining a cavity having an outer configuration of the lens 50 to be produced. The mold is then placed in a rotatable mold carrier. While the mold and the carrier are being spun, two copolymerizable materials having different indices of refraction are injected into the mold in a predetermined sequence to interdiffuse therein. In other words, differential mixing of the two copolymerizable materials occurs as the filling of the mold progresses to establish a concentration gradient, i.e. an index gradient. The speed of the mold rotation is reduced and the interdiffusing materials form a polymerization mixture which has an index of refraction that varies outwards from the axis of rotation as shown in FIGS. 4 or 8.

Figure 11:
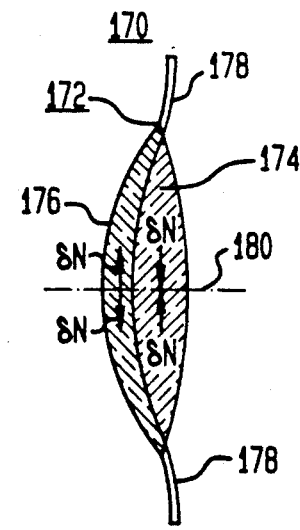
FIG. 11 is a cross-sectional view through the center of a doublet gradient index lens implant in accordance with the present invention.

Referring now to FIG. 11, there is shown an implant (intraocular lens) 170 in accordance with a fourth embodiment of the present invention. The implant 170 comprises an achromatic (corrected for color) doublet lens 172 formed of a first and a second element or shell 174 and 176, respectively. The first element 174 is convex-convex and is optically cemented (sealed, coupled) to the back of the second element 176 which is convex-concave. Each of the first and second elements 174 and 176 have radial gradient indices running in opposite directions. More particularly, the second element 176 has a gradient index profile where the highest index of refraction is located on an optical axis 180 of the lens 172 and decreases parabolically outwards towards the circumference of the lens 172. In contrast, the first element 174 has a gradient index profile where the highest index of refraction is located adjacent the circumference of the lens 172 and decreases parabolically inwards towards the axis 180. It is to be understood that the first and second elements 174 and 176 can have any suitable radial gradient profile which achieves the proper dual-focus intraocular lens 172 in accordance with the present invention. The implant 170 also includes haptics 178 of any suitable design which extend from the lens 172 and serve to engage the ciliary sulcus 32 for permanent fixation of the implant 170 behind the pupil 30 of the eyeball 20. The implant 170 employs the principle of a high dispersion for the first element 174 and low dispersion for the second element 176 to correct for chromatic aberration, i.e., a doublet lens of first and second element with decreasing and increasing indices of refraction, respectively.

It is to be appreciated and understood that the specific embodiments of the invention are merely illustrative of the general principles of the invention. Various modifications may be made consistent with the principles set forth. For example, an implant can be formed in any other configuration which includes at least one element or shell that has a radially deposited index gradient. Still further, in the second embodiment, the first and second elements 174 and 176, respectively, can be formed of the same or different transparent materials with the oppositely directed graded index of refraction. To compensate for a non-spherical cornea 24 (i.e., the cause of astigmatism), the gradient index lens (e.g., 50, 71, 91 or 170) may be cast anamorphic to compensate and correct for astigmatism. That is, the spin mold can have a non-spherical curvature to provide different powers in different zones to counter the distortion caused by a non-spherical cornea 24. Such intraocular lens would be an anamorphic gradient Index (GRIN) lens.

What is claimed is:

1. An intraocular lens for use in a human eyeball to replace a natural crystalline lens, said intraocular lens comprising:

a convex anterior surface and a convex posterior surface, each said surface having an outer edge;

an axis through said anterior and posterior surfaces;

a periphery at said outer edges of said anterior and posterior surfaces;

an inner zone and an outer zone, each said zone extended about sai axis between said anterior and posterior surfaces;

a first transparent material having a continuously varying gradient index of refraction of a first predetermined profile in said inner zone, the index of refraction in said inner zone decreasing in accordance said first profile in a direction away from said axis toward said periphery;

a second transparent material having a continuously varying gradient index of refraction of a second predetermined profile in said outer zone, the index of refraction in said outer zone decreasing in accordance with said second profile in a direction away from said axis toward said periphery; and means for engaging predetermined portions of the eyeball to hold said intraocular lens in place.

2. An intraocular lens according to claim 1 wherein said anterior and posterior surfaces of said inner zone each have a curvature which, in combination with said varying gradient index of refraction of said first material, causes rays of light from only nearby objects to be focused on a retina of an eyeball.

3. An intraocular lens according to claim 1 wherein said anterior and posterior surfaces of said outer zone each have a curvature which, in combination with said varying index of refraction of said second material, causes rays of light from only distant objects to be focused on a retina of an eyeball.

4. An intraocular lens according to claim 1 wherein said first and second predetermined profiles are parabolic.

* * * * *